United States Patent [19]

Kujawski

[11] Patent Number: 5,265,606
[45] Date of Patent: Nov. 30, 1993

[54] SYSTEM AND TECHNIQUE FOR MEASURING BLOOD CHARACTERISTICS BY CENTERING A SENSOR IN AN ARTERY

[75] Inventor: Dennis Kujawski, Brookline, N.H.

[73] Assignee: C. R. Bard, Inc., Murray Hill, N.J.

[21] Appl. No.: 23,174

[22] Filed: Feb. 25, 1993

Related U.S. Application Data

[63] Continuation of Ser. No. 557,133, Jul. 23, 1990, abandoned.

[51] Int. Cl.⁵ ............................................. A61M 37/00
[52] U.S. Cl. .................................... 128/632; 604/268; 604/280; 604/281
[58] Field of Search .............. 128/772; 604/21, 164, 604/165, 280, 281, 282, 283, 268

[56] References Cited

U.S. PATENT DOCUMENTS

| Re. 27,310 | 3/1972 | Hakim | 604/268 |
|---|---|---|---|
| 3,335,715 | 8/1967 | Hugenholtz et al. | 128/2 |
| 3,405,708 | 10/1968 | Webster, Jr. | 128/2.05 |
| 3,545,428 | 12/1970 | Webster, Jr. | 128/2.05 |
| 3,674,013 | 7/1972 | Polanyl | 128/634 |
| 3,807,390 | 4/1974 | Ostrowski et al. | 128/2.05 R |
| 3,918,456 | 11/1975 | Patel | 604/280 |
| 4,311,138 | 1/1982 | Sugarman | 604/21 |
| 4,576,772 | 3/1986 | Carpenter | 604/280 |
| 4,643,716 | 2/1987 | Drach | 604/281 |
| 4,733,669 | 3/1988 | Segal | 128/663 |
| 4,840,623 | 6/1989 | Quackenbush | 604/280 |
| 4,887,996 | 12/1989 | Bengmart | 604/280 |
| 4,925,445 | 5/1990 | Sakamoto et al. | 604/281 |
| 4,927,426 | 5/1990 | Dretler | 604/280 |

OTHER PUBLICATIONS

Pieper et al., "Catheter-Tip Gauge for Measuring Blood Flow Velocity and Vessel Diameter in Dogs", Journal of Applied Physiology, vol. 24, No. 2, Feb. 1968, pp. 259-261.

*Primary Examiner*—Peter A. Aschenbrenner
*Attorney, Agent, or Firm*—Wolf, Greenfield & Sacks

[57] ABSTRACT

A probe carrying sensor means at its distal tip is supported centrally within a blood vessel by an introducer catheter. The introducer catheter includes a percutaneously insertable shaft which is configured to engage and be supported by the inner luminal surface of the blood vessel. The distal tip of the catheter shaft is disposed along a central axis of the catheter such that when the catheter is disposed in the blood vessel, the distal tip will be disposed substantially along that axis and substantially in the center of the blood vessel lumen. The probe passed through the catheter thus will emerge from the distal outlet orifice of the catheter into the blood vessel at the central axis of the blood vessel.

28 Claims, 4 Drawing Sheets

SYSTEM AND TECHNIQUE FOR MEASURING BLOOD CHARACTERISTICS BY CENTERING A SENSOR IN AN ARTERY

This application is a continuation of application Ser. No. 07/557,133, filed Jul. 23, 1990, now abandoned.

FIELD OF THE INVENTION

This invention relates to a system for in vivo detection and measurement of selected parameters of a patient's blood, such as blood gas concentrations, pH and the like.

BACKGROUND OF THE INVENTION

Among the desirable medical diagnostic procedures is that of measuring certain characteristics of a patient's blood. In some such diagnostic procedures, it is preferable to monitor the patient's blood on a continuous basis. For example, continuous monitoring is desirable when measuring blood gas concentrations including concentrations of oxygen, carbon dioxide and pH level.

It is believed that substantial efforts have been made in the research and development of sensing devices that can be delivered to and placed directly in the patient's artery to expose the sensor to the blood flowing in that artery. Such continuous sensing directly in the artery is, in many cases, preferred to a batch processing in which a predetermined sample volume of blood is removed and is tested outside of the blood stream. Such batch processing does not provide real time monitoring of the patient's condition.

A variety of blood gas sensing devices have been proposed. Typically they are in the form of a probe that incorporates a light transmissive optical fiber having a sensing element at the distal end of the fiber. By way of example, a number of such sensing devices are described in "Progress in the Development of a Fluorescent Intravascular Blood Gas System Man", CK Mahutte et al., *Journal of Clinical Monitoring*, Vol. 6, No. 2, Apr. 1990, p. 147-157, the disclosure of which is hereby incorporated by reference in its entirety. Sensing devices for sensing pH, $PCO_2$ and $PO_2$ have been described in a number of publications including, for example, Gehrich, JL, Lubbers, DW, Opitz, N, et al., "Optical Fluorescence and Its Application to an Intravascular Blood Gas System", *IEEE Trans Biomed Eng*, 1986;2:117-132 and Miller, WW, Yafuso, M, Yan, CF, et al., "Performance of an In-Vivo Continuous Blood Gas Monitor with Disposable Probe", *Clin Chem* 1987;33:1538-1542. Reference is made to those publications for further illustrative description of such probes. Reference also is made to U.S. Pat. No. 4,800,886 issued Jan. 31, 1989; U.S. Pat. No. 4,861,727 issued Aug. 29, 1989; and U.S. Pat. No. 4,900,933 issued Feb. 13, 1990 for further descriptions of such probes.

Typically, it has been proposed to insert such blood gas sensor devices into an artery, such as into the radial artery, in the region of the wrist. Access to the radial artery is convenient in that it is common to catheterize hospital patients with a short catheter accessing the radial artery in order to measure the patient's blood pressure. It would be desirable to insert the probe carrying the sensor(s) through that same catheter, thus avoiding the necessity of making a second percutaneous puncture.

Although considerable progress is believed to have been made in the development of the technology of the sensors themselves, significant difficulties have been encountered in using such sensors to measure the blood parameters under investigation. Although it would be desirable to be able to measure the blood parameters directly and continuously within the artery, attempts to do so frequently have resulted in aberrant, erratic sensor values. A number of hypotheses have been developed to explain the cause of the aberrant sensor values, among which is one referred to in the Mahutte publication as the "wall effect", said to be caused by the sensor touching the blood vessel wall and hence resulting in a reading of an average of blood and tissue rather than of the blood alone. Also suggested as a possible cause for the aberrant sensor values has been clotting at the probe tip as well as the possibility that the sensed elements in the blood may be different in some patients at the wrist than it is at the left ventricle of the patient's heart. As described in Mahutte, it was discovered that when the probe tip was retracted within the delivery catheter and no longer touched the arterial wall, the aberrations in sensed values were eliminated. Retraction of the probe within the cannula tip, however, may cause other difficulties. In order to effect measurements with the tip retracted in the cannula, it is necessary to withdraw a sample of the blood within the cannula to contact the tip of the withdrawn sensor. Thus, the sensing is not continuous but, instead, is periodic as a "batch" of blood is drawn into the cannula into contact with the sensor. Additionally, retraction of the sensing probe within the catheter tip also interferes with fluid communication through the catheter and thus will have a damping effect on blood pressure readings.

It would be desirable, therefore, to provide an improved system by which the probe sensor may be placed within the artery so as to be presented to continuous flow of blood but in a manner in which the probe sensor is spaced substantially from the inner surface of the blood vessel wall, preferably at or very close to the center of the blood vessel lumen, thereby avoiding the "wall effect". It is among the objects of the invention to provide such a system.

SUMMARY OF THE INVENTION

The invention utilizes a modified form of introducer catheter that is constructed so as to locate the distal outlet tip of the introducer catheter centrally within the artery. Consequently, when the probe carrying the sensor(s) is advanced through the introducer catheter, the sensor at the tip of the probe will emerge from the distal tip of the catheter and will be located substantially centrally within the artery, away from the wall. More specifically, in accordance with the invention, the introducer catheter includes an elongate tubular body having a luer fitting at its proximal end. The catheter is formed so that at least a distal segment of the catheter is non linear, that is, it has portions that are disposed transversely of the central longitudinal axis of the catheter but in which the distal outlet tip of the catheter is disposed substantially along the central axis of the catheter. For example, in one embodiment, the catheter is formed in a zigzag pattern having successive bends alternating on opposite sides of the central axis of the catheter. When such a catheter is placed in the patient's artery, the bends on opposite sides of the central axis will engage the wall of the artery on opposite sides of the artery lumen thus tending to stabilize the catheter in the lumen with the central axis of the catheter extending generally along the longitudinal axis of the artery. The distal outlet tip, which is disposed at the central axis of the catheter will be positioned substantially at the central axis of the artery. The sensor at the end of the probe thus can be projected out of the distal tip of the catheter and be disposed substantially centrally within the artery, spaced from the arterial wall.

Other catheter configurations may be employed in the practice of the invention. For example, the distal segment of the catheter (or in the case of a short catheter, the entire length of the catheter) may be formed in a generally helical configuration in which the distal tip of the catheter extends radially inwardly of the helix and then axially along the central axis of the helix. When a catheter having such configuration is disposed in the artery, the helical portion of the catheter will center itself within the artery with the distal tip being located substantially along the central axis of the catheter and the artery. Thus, in this configuration, the distal tip of the catheter will direct and dispose the protruding sensor at a position spaced substantially from the wall of the artery.

In another aspect of the invention, the distal-most portion of the probe is of a reduced diameter and is smaller than the diameter at the distal outlet tip of the catheter, thus leaving an annular space between the probe and the catheter through which fluid communication may be established for the purpose of continuing blood pressure measurements and the like.

It is among the general objects of the invention to provide an improved technique for improving the reliability of readings of sensors in a blood vessel.

Another object of the invention is to provide an improved technique and system for centering a sensor substantially centrally within the lumen of an artery.

Another object of the invention is to provide an introducer catheter configured so that when the catheter is placed in a blood vessel, the distal outlet tip of the catheter will be disposed in spaced relation to the wall of the blood vessel, preferably substantially centrally within the lumen of the blood vessel.

A further object of the invention is to provide an introducer catheter having an irregular shape adapted to prevent the tip of the catheter from contacting the surface of the artery lumen.

DESCRIPTION OF THE DRAWINGS

The foregoing and other objects and advantages of the invention will be appreciated more fully from the following further description thereof with reference to the accompanying drawings wherein:

FIG. 5(a-c) are an enlarged diagrammatic cross-sectional illustration of the distal tip of a probe and an introducer catheter in accordance with the invention in which the probe and catheter configuration cooperates to permit blood pressure measurements to be made while the probe resides in the catheter;

DESCRIPTION OF THE PREFERRED EMBODIMENT

Figure 1:
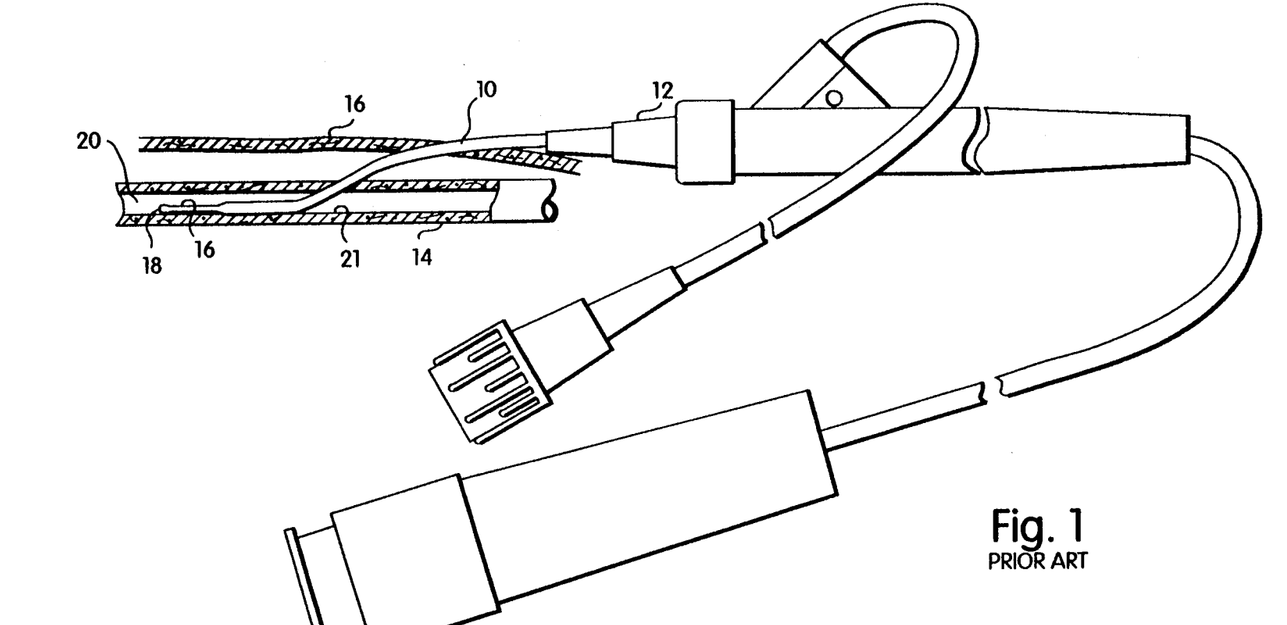
FIG. 1 is a somewhat diagrammatic illustration of a conventional introducer catheter inserted percutaneously into an artery with the sensor of a probe protruding from the tip of the catheter and contacting the wall of the artery.

FIG. 1 illustrates, diagrammatically, the manner in which a conventional short catheter is introduced percutaneously into an artery, such as the insertion of such a catheter into the radial artery to monitor a patient's blood pressure as well as to provide arterial access. The catheter typically includes an elongate flexible tubular shaft 10. The shaft may be considered as having a proximal end (outside of the patient) and a distal end (inside the patient). The catheter includes a fitting 12 attached to the proximal end of the shaft 10. The fitting 12 typically has a luer configuration so that it may be mated with fittings of other devices, such as other tubes, blood pressure monitoring devices and the like. The catheter typically is inserted into the artery 14 in a percutaneous procedure in which the catheter is mounted on a needle 13 (FIG. 1B) and together they are advanced through the skin to pierce the skin 16 and the wall of the artery. Once the distal end of the catheter has been advance into the artery 14, the needle 13 is withdrawn. The proximal end of the catheter typically is taped to the patient's skin to secure it in place.

FIG. 1 also illustrates, somewhat diagrammatically, a sensor assembly, of the type that may be used for blood gas sensing, inserted through the introducer catheter with the sensing tip 18 of the sensing probe 16 protruding from the distal end of the catheter shaft 10 into the lumen 20 of the artery. It will be appreciated from FIG. 1 that because the catheter shaft necessarily enters the artery at an angle, the distal end of the catheter shaft 10 will lie against the inner surface of the lumen 20 of the artery. Consequently, when the sensing probe 16 is advanced through the catheter and into the artery, the extending sensor tip 18 of the probe 16 will tend to lie closely adjacent or in direct contact with the inner luminal surface 21 of the arterial lumen. As described above, it is believed that the principal cause for erratic readings of blood gas sensing probes is the "wall effect" which results from the location of the probe in close proximity to or in contact with the luminal surface 20 of the artery.

Figure 2:
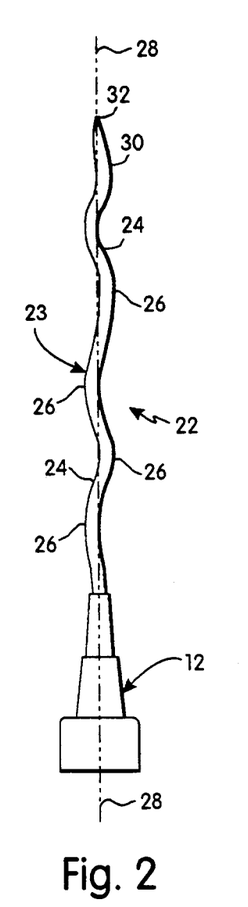
FIG. 2 is an enlarged side view of one embodiment of a catheter in accordance with the invention.
Figure 3:
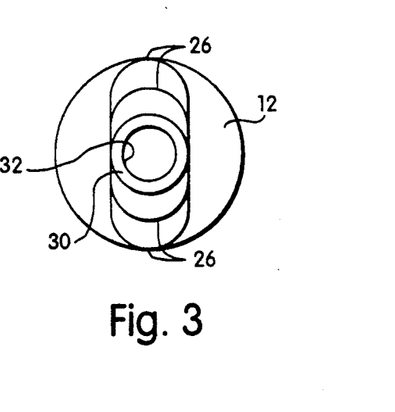
FIG. 3 is a greatly enlarged end view of a catheter as seen from the distal end of the catheter from the top in FIG. 2.
Figure 4:
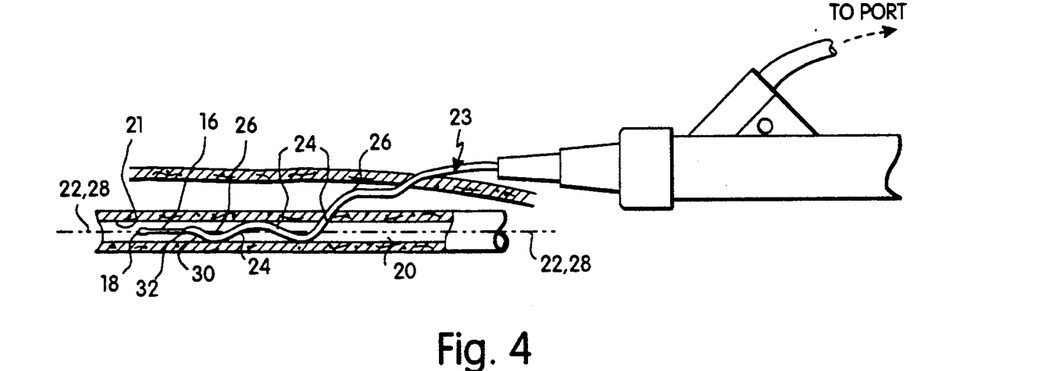
FIG. 4 is a diagrammatic illustration of the introducer catheter of FIGS. 2 and 3 inserted percutaneously into an artery and with a probe extending through and projecting distally from the end of the catheter.

FIGS. 2-4 illustrate one embodiment of the invention by which it is assured that the distal tip of the probe 16 at which the sensor 18 is carried, will be disposed substantially in the region of the central axis (suggested by the phantom line 22 in FIG. 4) of the lumen 20 of the artery. In this embodiment of the invention, the catheter shaft 23 is formed in a zig zag configuration including a plurality of segments 24 connected end to-end at bends or apices 26. The introducer catheter 23 may be considered as having a longitudinally extending central axis 28 with the apices 26 being spaced transversely from the central axis 28. The distal tip of the catheter shaft 23, however, is formed to lie substantially along the central axis 28 and includes a distal tip segment 30 that terminates in a distal outlet orifice 32. The tip segment 30 and outlet orifice 32 lie along the central axis 28.

Figure 1A:
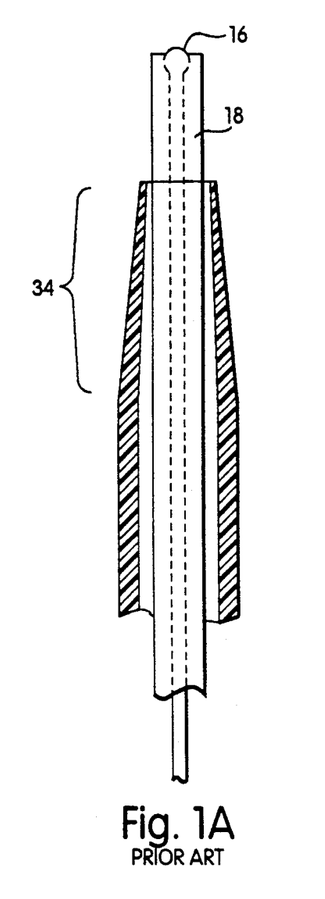
FIG. 1A is an enlarged cross-sectional, fragmented illustration of the distal tip of an introducer catheter and fiber optic probe of the type illustrated in FIG. 1.
Figure 1B:
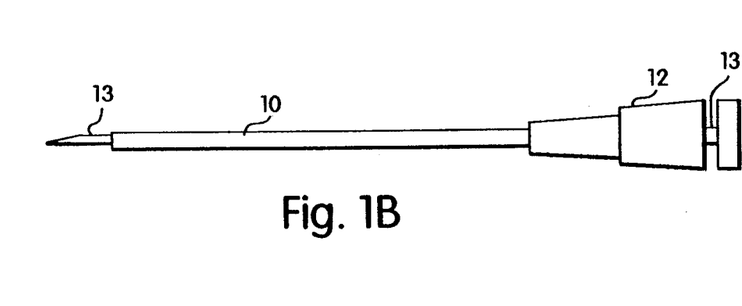
FIG. 1B is an illustration of an introducer catheter adapted for percutaneous insertion into a blood vessel mounted on a needle in readiness to be percutaneously inserted into the patient.

The introducer catheter of the type illustrated in FIGS. 2-4 includes a tubular shaft 23 that is formed from a flexible polymeric material, such as Teflon (polytetrafluoroethylene) or other suitable polymer conventionally used for catheter shafts. The polymer should be selected such that the catheter may be straightened temporarily so that it may be placed on the introducing needle as indicated in FIG. 1B. The polymer should have sufficient memory so that after the needle is withdrawn, the catheter will expand to assume its non linear (zig zag in FIGS. 2-4) configuration. The catheter should be dimensioned with respect to the intended artery in which it is to be placed such that the height of the apices 26 (measured transversely to the central axis 28) is at least as great as the inner diameter of the lumen 20 of the artery into which it is to be placed. Thus, a properly selected catheter so placed will expand within the artery as suggested in FIG. 4 so that the apices 26 engage the inner luminal surface 21 of the artery thereby centering and stabilizing the position of the catheter in the artery. The catheter will be centered in the artery with its central axis 28 being disposed substantially along the central axis 22 of the artery. Thus, the distal tip segment 30 and outlet orifice 32 of the introducer catheter will be disposed and extend substantially along the center of the artery lumen. Consequently, when the probe 16 carrying the sensor 18 is advanced through the introducer catheter, it will emerge from the outlet orifice 32, extending generally longitudinally of the artery and substantially centralized within the artery. The sensor tip thus is maintained in substantial spaced relation from the surface of the artery lumen 20, thereby avoiding the "wall effect" and development of aberrant readings.

As illustrated in FIGS. 2-4, the zig zag segments 24 lie substantially in a single plane. Such a planar configuration, however, is not essential and the zig zag segments could assume other configurations, such as a generally helical or twisted pattern. It may be noted that the height of the apices 26 may be substantially the same along the length of the catheter or, as suggested somewhat in FIGS. 2 and 3, the height of the apices may be decreased toward the distal end of the catheter, if desired.

Figure 5:
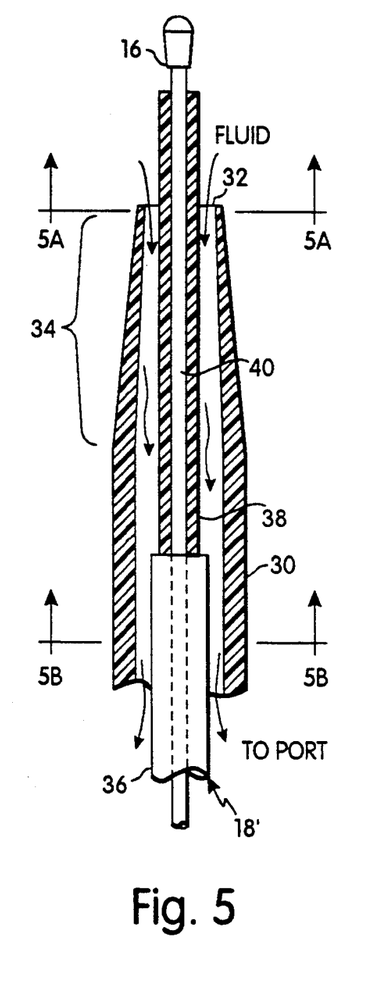
Figures 5A, 5B:
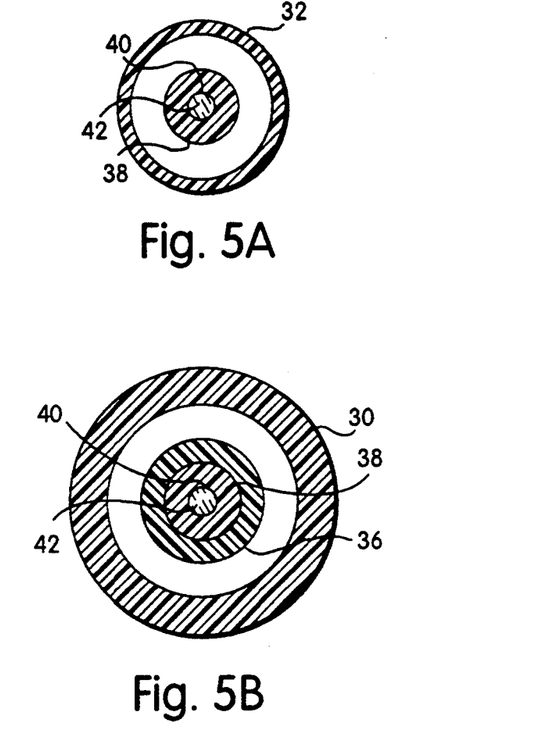
Figure 5C:
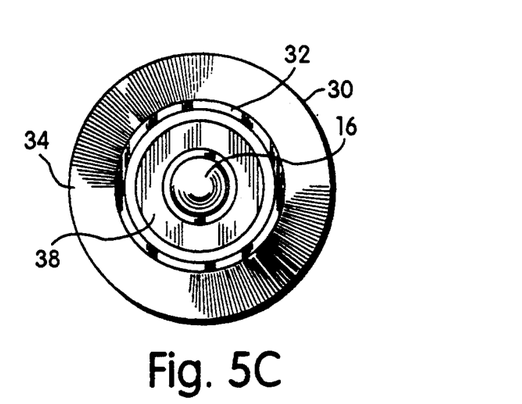

FIGS. 5A-5C illustrate another facet of the invention by which the introducer catheter may serve to centralize the sensing probe and in which the catheter maintains its fluid capability so as to permit monitoring of blood pressure while the probe remains in place in the introducing catheter. It may be noted, as illustrated in FIGS. 1A and 5 that the distal end of the catheter typically has a tapered segment 34 terminating in a distal outlet tip of reduced wall thickness and smaller diameter than the more proximal portions of the catheters. The purpose for such a tapered configuration is to enable the catheter to fit snugly onto the introducing needle so that when the introducing needle percutaneously pierces the skin and the blood vessel the catheter that is carried on the needle will not become snagged on the skin or the tissue of the blood vessel. The somewhat constricted distal tip, however, tends to constrict the remaining cross sectional flow area when a probe 16 extends through the device as suggested in FIG. 1A. In order to permit continued blood pressure monitoring capability, the present invention contemplates employing a sensor probe in which the distal tip of the sensor probe is of reduced diameter. Thus, as illustrated in FIG. 5, the probe 18' may have a more proximal segment 36 having a larger diameter while a distal segment 38 of the probe may have a reduced diameter. It is intended that the distal segment 38 extends through the distal portion and the orifice 32 of the catheter shaft. The reduced diameter of the distal segment 38 does not adversely restrict the flow area through the distal tip of the catheter thereby permitting continued blood pressure measurements even when the probe is in place. The stepped diameter for the probe may be formed by varying the thickness and diameter of the jacket(s) 40 that encase the optical fiber 42 that extends through the probe.

Figure 6:
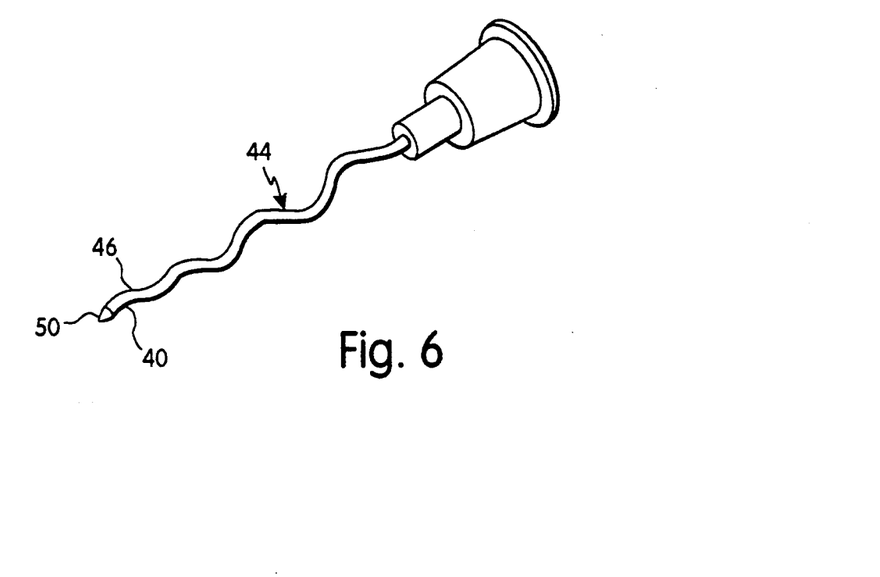
FIG. 6 is an illustration of another embodiment of an introducer catheter in accordance with the invention.
Figure 7:
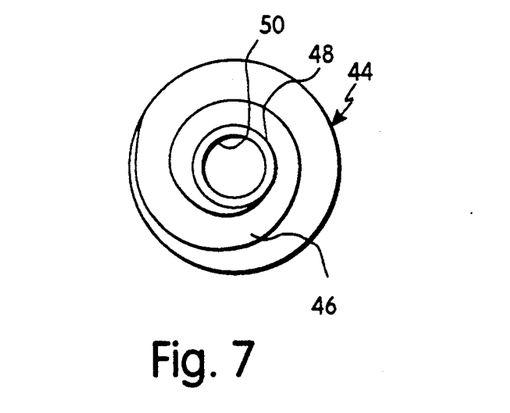
FIG. 7 is an end view of the catheter of FIG. 6.

As mentioned above, the configuration of the introducer catheter is not limited to the embodiment as shown and may take other forms. For example, still another configuration is that illustrated in FIGS. 6 and 7 in which the introducer catheter shaft 44 is formed in a general helical coil pattern. As in the previous embodiment, the distal end 46 of the catheter shaft extends radially inwardly toward the central axis of the device and terminates in a distal tip segment 48 and distal outlet orifice 50 that lie along the central axis. In this embodiment, the helically coiled catheter shaft is selected to have a diameter slightly greater than the inner luminal diameter of the blood vessel into which it is to be placed so that when the carrying introducing needle is removed and the catheter expands to its helically coiled configuration, it will expand into firm, supported engagement with the inner surface of the artery lumen.

It will be appreciated that still other configurations for the introducer catheter may be provided that will engage the inner luminal surface of the artery to stabilize the catheter within the artery and in which the distal of the catheter includes a distal tip segment which extends along the central axis of the catheter and has a distal outlet orifice through which the distal tip of the sensing probe may emerge, extending longitudinally of and centrally within the lumen of the blood vessel.

Thus, it will be appreciated that the invention provides a means and a technique by which a sensing probe may be positioned centrally within the blood vessel and in which the probe is maintained in substantially spaced relation from the luminal surface of the blood vessel thereby avoiding the "wall effect". Consequently the invention enables blood parameters, such as blood gas concentrations and pH levels to be sensed in vivo, directly in the flowing blood stream without requiring removal of discrete batches for testing outside of the blood stream.

It should be understood, however, that the foregoing description of the invention is intended merely to be illustrative thereof and that other embodiments, modifications and equivalents may be apparent to those skilled in the art without departing from its spirit.

Having thus described the invention what I desire to claim and secure by Letters Patent is:

1. A percutaneously insertable, needle mountable introducer catheter for guiding and supporting a probe within a blood vessel, in combination with a probe, comprising:

a tubular elongate flexible catheter shaft having a fitting at a proximal end and a distal tip segment that terminates in an outlet orifice, the tip segment being no greater in diameter than the shaft;

the inner and outer surfaces of the catheter shaft and tip segment being substantially smooth;

the catheter having a longitudinally extending central axis that extends through the fitting and the outlet orifice;

a portion of the shaft extending between the fitting and the outlet orifice including at least external portions of the shaft that are spaced transversely from the central axis at a distance sufficient for surfaces of the external portions to engage the inner luminal surface of the blood vessel to stabilize the transverse position of the catheter within the blood vessel relative to the longitudinal axis of the blood vessel; and the distal tip segment extending substantially along the central axis; and a probe constructed to be passed through the catheter shaft without substantially distorting said stabilizing portion of the catheter shaft, whereby the distal end of the probe may protrude beyond the distal outlet orifice substantially along said central axis.

2. An introducer catheter and probe as defined in claim 1 wherein the catheter shaft is formed in a longitudinally extending zig-zag configuration including alternating substantially opposed apices and segments of the shaft and where the apices are displaced transversely from the central axis of the catheter.

3. An introducer catheter and probe as defined in claim 1 wherein the shaft is formed to include a longitudinally extending helically coiled segment of the shaft, the central axis extending through the helical coil.

4. An introducer catheter and probe as defined in any one of claims 1-3 wherein the catheter is sufficiently flexible to be mounted on a straight rigid needle, the shaft comprising a polymeric material having memory such that when the needle is withdrawn from a shaft, the shaft will assume said configuration in which at least external portions of the shaft are spaced transversely from the central axis of the catheter.

5. An introducer catheter and probe as defined in claim 4 further comprising, in combination with said needle;

said introducer catheter being mounted on said needle.

6. An introducer catheter and probe as defined in claim 2 wherein the apices are spaced at a substantially uniform height from the central axis of the catheter.

7. An introducer catheter and probe as defined in claim 2 wherein at least some of more distally disposed apices are spaced closer to the central axis of the catheter than apices at more proximal portions of the catheter shaft.

8. An introducer catheter and probe as defined in any one of claims 1-3, 6 or 7 wherein a top segment of the catheter shaft is tapered in a distal direction.

9. An introducer catheter and probe as defined in claim 8, the probe having a reduced diameter at a distal tip thereof, said reduced diameter being significantly smaller than the outlet orifice.

10. A method for supporting a probe within a blood vessel at a location spaced from the luminal surface of the blood vessel comprising:

providing a catheter having:

a tubular elongate flexible catheter shaft having a fitting at a proximal end and a distal tip segment that terminates in an outlet orifice;

the catheter having a longitudinally extending central axis that extends through the fitting and the outlet orifice;

a portion of the shaft extending between the fitting and the outlet orifice including at least external portions of the shaft that are spaced transversely from the central axis at a distance sufficient for surfaces of the external portions to engage the inner luminal surface of the blood vessel to stabilize the transverse position of the catheter within the blood vessel relative to the longitudinal axis of the blood vessel; and the distal tip segment extending substantially along the central axis; and inserting the catheter into the blood vessel to cause the catheter to become stabilized so as to limit transverse movement of the catheter shaft in the blood vessel relative to a longitudinal axis of the blood vessel; and thereafter advancing a probe through the catheter so that its distal tip emerges from the distal outlet orifice of the catheter in a spaced apart relationship from the inner luminal surface of the blood vessel.

11. An introducer catheter for placing a probe in substantial alignment with the central longitudinal axis of a blood vessel, in combination with said probe, comprising:

a tubular elongate flexible catheter shaft having a proximal end carrying a fitting and having a distal tip segment that terminates in an outlet orifice;

the catheter defining a longitudinally extending central axis that extends through the fitting and the outlet orifice, wherein the distal tip segment extends substantially along the central axis; and the shaft being made of a material having a shape memory and including shaft portions spaced from the central axis for centering the distal tip segment of the shaft relative to a blood vessel lumen, wherein the shaft portions can be straightened in substantial alignment with the central axis when the shaft is mounted over a rigid needle to facilitate insertion of the shaft into a blood vessel lumen; and a probe constructed to be passed through the catheter shaft without substantially distorting said shaft portions, whereby the distal end of the probe may protrude beyond the distal outlet orifice of the catheter substantially along said central axis.

12. An introducer catheter and probe as defined in claim 11 wherein the means for centering includes at least two longitudinally remote zig-zag formations upon the shaft having apices that are displaced transversely from the central axis.

13. An introducer catheter and probe as defined in claim 11 wherein the means for centering includes a helically coiled shaft segment, the central axis extending through the helically coiled segment.

14. An introducer catheter and probe as defined in any one of claims 11-13 wherein the shaft comprises a polymeric material and is sized to be mounted on a straight rigid needle such that when mounted on the needle the shaft assumes a straightened shape and when removed therefrom assumes an original non-straightened shape that includes the means for centering.

15. An introducer catheter and probe as defined in any one of claims 11-13 further comprising the probe having a reduced diameter at a distal tip thereof, said reduced diameter being significantly smaller than the outlet orifice.

16. A percutaneously insertable, introducer catheter for aligning a probe within a blood vessel away from the inner luminal surface of the blood vessel and substantially along a longitudinal axis of the blood vessel, and a probe in combination therewith, comprising:

a tubular elongate flexible catheter shaft having a proximal end carrying a fitting and a distal tip segment that terminates in an outlet orifice, the tip segment being no greater in diameter than the shaft;

the inner and out surfaces of the catheter shaft and tip segment being substantially smooth;

the catheter having a longitudinally extending central axis that extends through the fitting and the outlet orifice, wherein the distal tip segment extends substantially along the central axis; and the shaft including shaft portions extending transversely from the central axis for contacting at least two longitudinally spaced and circumferentially opposed portions of the inner luminal surface of a blood vessel to stabilize the catheter within the blood vessel radially relative to the longitudinal axis of the blood vessel; and a probe constructed to be passed through the catheter shaft without substantially distorting said stabilizing portion of the catheter shaft, whereby the distal end of the probe may protrude beyond the distal outlet orifice substantially along said central axis.

17. A percutaneously insertable, needle mountable introducer catheter for substantially centering a probe relative to the longitudinal axis of a blood vessel and removing the probe from contact with the inner luminal surface of the blood vessel, and a probe in combination therewith, comprising:

a tubular elongate flexible catheter shaft having a proximal end carrying a fitting and a distal tip segment that terminates in an outlet orifice, the tip segment being no greater in diameter than the shaft;

the inner and outer surfaces of the catheter shaft and tip segment being substantially smooth;

the catheter having a longitudinally extending central axis that extends through the fitting and the outlet orifice;

the shaft comprising linear segments substantially aligned with the central axis and a plurality of longitudinally spaced non-linear segments having external surfaces that extend transversely from the central axis beyond an outer diameter of the linear segments in substantially opposing directions; and the distal tip segment extending in substantial alignment with the central axis and between the opposed non-liner segments; and a probe constructed to be passed through the catheter shaft without substantially distorting said non-linear segments of the catheter shaft, whereby the distal end of the probe may protrude beyond the distal outlet orifice substantially along the central axis.

18. An introducer catheter and probe as defined in claim 17 wherein the non-linear segments comprise a plurality of coplanar zig-zags.

19. An introducer catheter and probe as defined in claim 17 wherein the non-linear segments comprise portions of a helical coil.

20. An introducer catheter and probe as defined in any one of claim 17-19 wherein the shaft comprises a polymeric material having memory and being sized to be mounted on a straight rigid needle such that when mounted on a needle the shaft assumes a straightened shape and when removed therefrom assumes an original non-straightened shape including the non-linear segments.

21. An introducer catheter and probe as defined in any one of claims 17-19 wherein a tip of the catheter shaft is tapered in a distal direction.

22. An introducer catheter and probe as defined in claim 21 further comprising said probe having a reduced diameter at a distal tip thereof, said reduced diameter being significantly smaller than an inner diameter of the outlet orifice.

23. A method for positioning a probe within a blood vessel at a location spaced from the inner luminal surface of the blood vessel comprising:

providing an introducer catheter having a longitudinally extending central axis and a distal tip segment that lies along the central axis and terminates in an outlet orifice, the catheter having a tubular elongate flexible shaft of a material having shape memory including eternal portions that extend to contact the inner luminal surface of the blood vessel at a plurality of points to stabilize a distal tip segment of the shaft transversely relative to a longitudinal axis of the blood vessel so that a probe emanating from the distal tip segment is out of contact with the luminal surface and is disposed longitudinally relative to the blood vessel;

mounting the introducer catheter on a rigid needle so that the external portions of the shaft becomes substantially straight;

inserting the straightened shaft and needle through a blood vessel wall and into a blood vessel lumen;

removing the rigid needle from the shaft following insertion so that the catheter becomes transversely stabilized in the blood vessel; and inserting a probe through the shaft so that it emerges from the distal tip segment of the catheter in a spaced apart relationship from the luminal surface of the blood vessel.

24. A percutaneously insertable, needle mountable introducer catheter for supporting a probe within a blood vessel at a location spaced from the inner luminal surface of the blood vessel, in combination with a probe, comprising:

a tubular elongate flexible catheter shaft having a proximal end, a longitudinally extending central axis, and a distal tip segment that terminates in an outlet orifice, the tip segment being no greater in diameter than the shaft;

the inner and outer surfaces of the catheter shaft being substantially smooth;

means comprising portions of the shaft and defining a plurality of spatially opposed support points spaced longitudinally along the shaft, the support points disposed transverse to the central axis so as to orient the distal tip segment in a substantially spaced apart relationship from the inner luminal surface of the blood vessel;

so that a probe emanating from the outlet orifice extends longitudinally in a spaced apart relationship from the inner luminal surface of the blood vessel; and a probe constructed to be passed through the catheter shaft without substantially distorting said support points, whereby the distal end of the probe may protrude beyond the distal outlet orifice substantially along said central axis.

25. An introducer catheter for supporting a probe mounted therein away from the inner luminal surface of a blood vessel having deployed and undeployed positions, in combination with a probe, comprising:

a tubular elongate flexible catheter shaft having a proximal end, a longitudinally extending central axis, and a distal tip segment that lies along the central axis and terminates in an outlet orifice;

a plurality of non-linear segments of the shaft being disposed transverse to the central axis so that in a deployed position within the blood vessel the segments engage circumferentially opposed portions of the inner luminal surface of the blood vessel with the distal tip segment supported by the segments away from the inner luminal surface of the blood vessel and wherein a probe passed through the shaft emerges from the outlet orifice extending spaced from the inner luminal surface in substantial longitudinal alignment with a line through the proximal end and the distal tip segment; and the shaft being sized to accept a needle that causes the non-linear segments to become straightened in alignment with the needle in an undeployed position, a combination of the shaft and the needle being easily insertable into a blood vessel it he undeployed position and the needle being removable from the shaft subsequent to insertion to place the shaft in the deployed position; and a probe constructed to be passed through the catheter shaft without substantially distorting said non-linear segments, whereby the distal end of the probe may protrude beyond the distal outlet orifice substantially along the central axis.

26. A percutaneously insertable, needle mountable introducer catheter for supporting a probe in a spaced apart relationship from the inner luminal surface of a blood vessel without substantial reduction of blood flow therearound in the blood vessel, in combination with a probe, comprising:

a tubular elongate flexible catheter shaft having a proximal end, a longitudinally disposed central axis, and a distal tip segment that lies along the central axis and terminates in an outlet orifice sized to support a probe therefrom, the shaft having a diameter substantially smaller than that of a blood vessel into which the shaft may be inserted so as not to substantially impede blood flow through the blood vessel, the tip segment being no greater in diameter than the shaft;

the inner and outer surfaces of the shaft and tip segment being substantially smooth;

the shaft including portions extending transversely from the central axis for engaging the inner luminal surface of the blood vessel at a plurality of circumferentially opposed points to support the distal tip segment at a distance from the inner luminal surface so that a probe passed from the outlet orifice remains in a spaced apart relationship from the inner luminal surface; and a probe constructed to be passed through the catheter shaft without substantially distorting said transversely extending portions of the catheter shaft, whereby the distal end of the probe may protrude beyond the distal outlet orifice substantially along the central axis.

27. An introducer catheter and probe as defined in claim 1 wherein the catheter shaft has a predetermined cross-sectional radius and wherein the distance by which said external portions of the shaft are spaced transversely from the central axis of the catheter is greater than said predetermined radius.

28. A percutaneously insertable, needle mountable introducer catheter for guiding and supporting a probe within a blood vessel, and probe in combination, comprising:

a tubular elongate flexible catheter shaft having a proximal end and a distal end and having a predetermined cross-sectional radius;

the shaft having a fitting at its proximal end and a distal tip segment that terminates in an outlet orifice, the tip segment being no greater in diameter than the shaft;

the inner and outer surfaces of the catheter being substantially smooth;

the catheter having a longitudinally extending central axis that extends through the fitting and the outlet orifice;

a portion of the shaft extending between the fitting and the outlet orifice including portions that are spaced transversely from the central axis a distance greater than said predetermined radius thereby to enable said transversely spaced portions to engage the inner luminal surface of the blood vessel to stabilize the transverse position of the catheter within the blood vessel relative to the longitudinal axis of the blood vessel; and the distal tip segment extending substantially along the central axis;

whereby the distal tip segment will be oriented so that a probe passed trough the catheter will emerge from the outlet orifice extending longitudinally of and substantially along the central axis; and the probe constructed to be passed through the catheter shaft without substantially distorting said transversely extending portions of the catheter shaft, whereby the distal end of the probe may protrude beyond the distal outlet orifice substantially along the central axis.

* * * * *